US012170848B2

(12) United States Patent
Donaldson et al.

(10) Patent No.: US 12,170,848 B2
(45) Date of Patent: Dec. 17, 2024

(54) HIGH ACCURACY DISPLACEMENT DEVICE (71) Applicant: Magic Leap, Inc., Plantation, FL (US)

(72) Inventors: Nick Donaldson, Plantation, FL (US); Changxin Yan, Santa Clara, CA (US); Ankur Gupta, San Francisco, CA (US); Vikram Chauhan, San Diego, CA (US)

(73) Assignee: Magic Leap, Inc., Plantation, FL (US)

(*) Notice: Subject to any disclaimer, the term of this patent is extended or adjusted under 35 U.S.C. 154(b) by 74 days.

(21) Appl. No.: 17/996,332

(22) PCT Filed: Apr. 16, 2021

(86) PCT No.: PCT/US2021/027752
§ 371 (c)(1),
(2) Date: Oct. 14, 2022

(87) PCT Pub. No.: WO2021/212016
PCT Pub. Date: Oct. 21, 2021

(65) Prior Publication Data
US 2023/0224591 A1    Jul. 13, 2023

Related U.S. Application Data

(60) Provisional application No. 63/011,106, filed on Apr. 16, 2020.

(51) Int. Cl.
*H04N 23/695*    (2023.01)
*G03B 17/56*    (2021.01)

(52) U.S. Cl.
CPC ......... *H04N 23/695* (2023.01); *G03B 17/561* (2013.01)

(58) Field of Classification Search
CPC ..... H04N 23/695; G03B 17/561; G06F 3/011; A61B 2017/00398; A61B 90/50;
(Continued)

(56) References Cited

U.S. PATENT DOCUMENTS

2005/0264777 A1* 12/2005 Gardner ............. G03F 7/70275
355/53
2005/0280903 A1* 12/2005 Oshima ................ G02B 7/102
359/697
(Continued)

FOREIGN PATENT DOCUMENTS

CN       104964134 A    10/2015
CN       106003155 B    12/2017
(Continued)

OTHER PUBLICATIONS

International Search Report & Written Opinion in International Appln. No. PCT/US2021/027752, mailed on Jul. 12, 2021, 12 pages.
(Continued)

*Primary Examiner* — Usman A Khan
(74) *Attorney, Agent, or Firm* — Fish & Richardson P.C.

(57) ABSTRACT

Devices are described for high accuracy displacement of tools. In particular, embodiments provide a device for adjusting a position of a tool. The device includes a threaded shaft having a first end and a second end and a shaft axis extending from the first end to the second end, a motor that actuates the threaded shaft to move in a direction of the shaft axis. In some examples, the motor is operatively coupled to the threaded shaft. The device includes a carriage coupled to the camera, and a bearing assembly coupled to the threaded shaft and the carriage. In some examples, the bearing assembly permits a movement of the carriage with respect to the threaded shaft. The movement of the carriage allows the position of the camera to be adjusted.

19 Claims, 5 Drawing Sheets

(58) Field of Classification Search
CPC ........ A61B 2090/365; A61B 2090/502; A61B 90/361; A61B 34/20; G02B 2027/0138; G02B 27/0176
USPC ........................................................ 348/373
See application file for complete search history.

(56) References Cited

U.S. PATENT DOCUMENTS

| | | | |
|---|---|---|---|
| 2006/0072020 A1* | 4/2006 | Mccutchen | G03B 17/02 348/E5.025 |
| 2009/0056158 A1 | 3/2009 | Tada et al. | |
| 2011/0018972 A1* | 1/2011 | Pan | H04N 13/296 348/47 |
| 2015/0146090 A1* | 5/2015 | Feinbloom | H04N 23/50 348/370 |
| 2015/0146091 A1* | 5/2015 | Feinbloom | G03B 17/566 348/370 |
| 2018/0217349 A1 | 8/2018 | Jin et al. | |

FOREIGN PATENT DOCUMENTS

| | | | |
|---|---|---|---|
| CN | 108363413 A | | 8/2018 |
| CN | 110159901 A | | 8/2019 |
| CN | 110329180 A | * | 10/2019 |
| CN | 209782070 U | * | 12/2019 |
| KR | 101164427 B1 | | 7/2012 |
| KR | 20160111750 A | | 9/2016 |

OTHER PUBLICATIONS

Extended European Search Report in European Appln. No. 21788193.7, dated Apr. 22, 2024, 8 pages.

* cited by examiner

HIGH ACCURACY DISPLACEMENT DEVICE

BACKGROUND

Virtual environments present a user with three-dimensional computer-generated images that are perceived in the same way as real images are perceived. That is, the user perceives a three-dimensional computer-generated image depending on the position of the image and her or his direction of view. The images are generated based on the position and orientation of the user (e.g., the head of the user) in space. This position can be tracked by spatial sensors, cameras, or a combination of both. In augmented reality (AR), three-dimensional computer-generated images overlay the real environment as perceived by the user. Any slight error in the tracking of the user or the positioning of the computer-generated images can result in a wrong perspective that can lead to misalignment of the computer-generated images with respect to the real environment. Thus, it may be desirable to minimize or eliminate positioning and tracking errors in AR systems.

SUMMARY

Embodiments of the present disclosure are generally directed to high accuracy displacement devices. More specifically, embodiments are directed to at least one apparatus and/or at least one system for adjusting a position of a camera or a sensor. The apparatus and/or system can include a threaded shaft, a motor, a carriage, and a bearing assembly.

One aspect of the present disclosure features a device for adjusting a position of a camera. The device can include a threaded shaft having a first end and a second end and a shaft axis extending therebetween; a motor that actuates the threaded shaft to move in a direction of the shaft axis, the motor being operatively coupled to the threaded shaft, a carriage coupled to the camera; and a bearing assembly coupled to the threaded shaft and the carriage, the bearing assembly permitting a movement of the carriage with respect to the threaded shaft, wherein the movement of the carriage allows the position of the camera to be adjusted.

Embodiments can optionally include one or more of the following features.

In some embodiments, the threaded shaft is a screw. In some embodiments, the screw is a fine adjustment screw.

In some embodiments, the fine adjustment screw includes about 80 to about 100 threads per inch.

In some embodiments, the device includes a positional accuracy of the camera of about 0.1 micrometers ($\mu$m) to about 1 $\mu$m.

In some embodiments, the bearing assembly includes a first bearing and a second bearing attaching the threaded shaft to a linear bearing coupled to the carriage, thereby enabling rotation of the carriage.

In some embodiments, a stabilizer bar couples the linear bearing to the carriage.

In some embodiments, the bearing assembly includes a third bearing and a fourth bearing axially attached to the threaded shaft, the third and fourth bearings configured to enable rotation of the threaded shaft while reducing friction between an outer surface of the threaded shaft and an inner surface of the third and fourth bearings.

In some embodiments, the camera is removably coupled to a bracket of the carriage.

In some embodiments, the bearing assembly includes a spring for biasing the bearing assembly along the shaft axis, the spring being generally coaxial with the shaft.

In some embodiments, the device further includes a thrust bearing coupling the threaded shaft to the spring.

In some embodiments, the threaded shaft is spring-loaded in an axial direction against a surface of the bearing assembly.

In some embodiments, the position of the one or more cameras includes an angular position, a linear position with respect to the shaft axis, or a combination thereof.

In some embodiments, the motor actuates the threaded shaft to rotate with respect to a camera axis, the camera axis perpendicularly traversing the shaft axis.

In some embodiments, the device further includes a threaded nut coupling the threaded shaft to the carriage.

Another aspect of the present disclosure features a device for adjusting a position of one or more cameras. The device can include a first and second threaded shafts having a first end and a second end and a shaft axis extending therebetween; a first and second motors that actuate the first and second threaded shafts to move in a direction of the shaft axis, the first and second motors being operatively coupled to the first and second threaded shafts; a carriage coupled to the one or more cameras; and a first and second bearing assemblies coupled to the first and second threaded shafts and the carriage, the first and second bearing assemblies permitting a movement of the carriage with respect to the first and second threaded shafts, wherein the movement of the carriage allows the position of the one or more cameras to be adjusted.

In some embodiments, the first and second threaded shafts are first and second screws.

In some embodiments, the first and second screws are fine adjustment screws.

In some embodiments, the fine adjustment screws include about 80 to about 100 threads per inch.

In some embodiments, the device includes a positional accuracy of the camera of about 0.1 micrometers ($\mu$m) to about 1 $\mu$m.

In some embodiments, the first and second bearing assemblies include a first bearing and a second bearings attaching the first and second threaded shafts to a linear bearing coupled to the carriage, thereby enabling rotation of the carriage.

In some embodiments, a stabilizer bar couples the linear bearing to the carriage.

In some embodiments, the first and second bearing assemblies include a third bearing and a fourth bearing axially attached to the first and second threaded shafts, the third and fourth bearings configured to enable rotation of the first and second threaded shafts while reducing friction between an outer surface of the first and second threaded shafts and an inner surface of the third and fourth bearings.

In some embodiments, the one or more cameras are removably coupled to a bracket of the carriage.

In some embodiments, the first and second bearing assemblies include a spring for biasing the first and second bearing assemblies along the shaft axis, the spring being generally coaxial with the first and second threaded shafts.

In some embodiments, the device further includes a thrust bearing attaching the first and second threaded shafts to the spring.

In some embodiments, the first and second threaded shafts are spring-loaded in an axial direction against a surface of the first and second bearing assemblies.

In some embodiments, the position of the one or more cameras includes an angular position, a linear position with respect to the shaft axis, or a combination thereof.

Another aspect of the present disclosure features an automated system for adjusting a position of a camera. The automated system can include a device including: a threaded shaft having a first end and a second end and a shaft axis extending therebetween; a motor that actuates the threaded shaft to move in a direction of the shaft axis, the motor being operatively coupled to the threaded shaft; a carriage coupled to the camera, a bearing assembly coupled to the threaded shaft and the carriage, the bearing assembly permitting a movement of the carriage with respect to the threaded shaft, wherein the movement of the carriage allows the position of the camera to be adjusted; and a computing device comprising a processor operatively coupled to the device, and a non-transitory computer readable storage medium with a computer program including instructions executable by the processor causing the processor to: i) calculate a displacement of the threaded shafts along the shaft axis that results in a desired position of the camera along the shaft axis, and ii) output the displacement of the threaded shaft to the motor.

In some embodiments, the position of the camera includes an angular position defining an initial angle of the camera.

In some embodiments, the position of the camera includes a linear position with respect to the shaft axis.

In some embodiments, the processor further calculates a desired angle of the camera relative to the initial angle of the camera based on the displacement of the threaded shaft.

In some embodiments, the processor further calculates a desired linear position of the camera relative to an initial linear position of the camera based on the displacement of the threaded shaft.

In some embodiments, the threaded shaft is a screw.

In some embodiments, the screw is a fine adjustment screw.

In some embodiments, the fine adjustment screw includes about 80 to about 100 threads per inch.

In some embodiments, the device includes a positional accuracy of the camera of about 0.1 micrometers (μm) to about 1 μm.

In some embodiments, the bearing assembly includes a first bearing and a second bearing attaching the threaded shaft to a linear bearing coupled to the carriage, thereby enabling rotation of the carriage.

In some embodiments, a stabilizer bar couples the linear bearing to the carriage.

In some embodiments, the bearing assembly includes a third bearing and a fourth bearing axially attached to the threaded shaft, the third and fourth bearings configured to enable rotation of the threaded shaft while reducing friction between an outer surface of the threaded shaft and an inner surface of the third and fourth bearings.

In some embodiments, the camera is removably coupled to a bracket of the carriage.

In some embodiments, the bearing assembly includes a spring for biasing the bearing assembly along the shaft axis, the spring being generally coaxial with the shaft.

In some embodiments, the system further includes a thrust bearing coupling the threaded shaft to the spring.

In some embodiments, the threaded shaft is spring-loaded in an axial direction against a surface of the bearing assembly.

It is appreciated that aspects and features in accordance with the present disclosure can include any combination of the aspects and features described herein. That is, aspects and features in accordance with the present disclosure are not limited to the combinations of aspects and features specifically described herein, but also include any combination of the aspects and features provided.

The use of the term "about," as used herein, refers to an amount that is near the stated amount by about 10%, 5%, or 1%, including increments therein. For example, "about" can mean a range including the particular value and ranging from 10% below that particular value and spanning to 10% above that particular value.

The details of one or more embodiments of the present disclosure are set forth in the accompanying drawings and the description below. Other features and advantages of the present disclosure will be apparent from the description and drawings, and from the claims.

DETAILED DESCRIPTION

One of the main sources of errors in tracking a position and/or an orientation of a user in AR systems, comes from the flexibility of the AR systems impacting the sensor-to-sensor rigid relationship (e.g., the six degrees of freedom (6DoF) transformation between sensors, known as extrinsics). In order to prevent this source of error, there is a need to simulate a real life scenario where the sensors are being deformed while the AR system is being used. Knowing the exact deformation of each sensor (i.e., ground truth extrinsics) at each time is critical for this evaluation. The devices and systems of the disclosure provide a way to both deform and also record the deformation with high accuracy (e.g., high micron and arcminute accuracy) at the same time while the AR system is being actively used.

Embodiments of the present disclosure are directed to high accuracy displacement devices and systems. In particular, embodiments provide a device that performs a high accuracy displacement of a camera or a sensor that may be mounted onto the body of the device. In some embodiments, a distinct advantage of a high accuracy displacement device is that it can reduce or eliminate potential tracking and/or positioning errors in augmented reality (AR) systems. The displacement devices consistent with this disclosure can control the position, the angle, or both of mounted tools (e.g., sensors, cameras, or a combination of both) with high accuracy. For example, the high accuracy displacement devices of the disclosure are capable of sub-arcminute deformations in rotation and sub-millimeter deformations in translated of mounted tools (e.g., sensors, cameras, or a combination of both) that can further be part of or be a wearable device. Current methods of positioning tools used in AR systems (e.g., sensors or cameras) achieve accuracy in arcminute and sub-millimeter scales; however, these methods use displacement devices that are typically large, heavy, and costly, which are generally used in photonics applications and are not amenable to be used as part of a portable and/or wearable device or system (e.g., an AR device or system). In some embodiments, an additional advantage of the high accuracy displacement devices of the disclosure is their compact, lightweight, and affordability characteristics that enable them to be portable or part of a portable device or system (e.g., an AR device or system or a robotic arm). Furthermore, current displacement devices that can achieve arcminute and millimeter deformations can typically only provide either rotational or displacement deformations. In contrast, in some embodiments, the high accuracy displacement devices of the disclosure provide both rotational and displacement deformations that can be simultaneously actuated and controlled. In some embodiments, the high accuracy displacement devices of the disclosure can be part of a portable and/or wearable data collection system.

Figure 1:
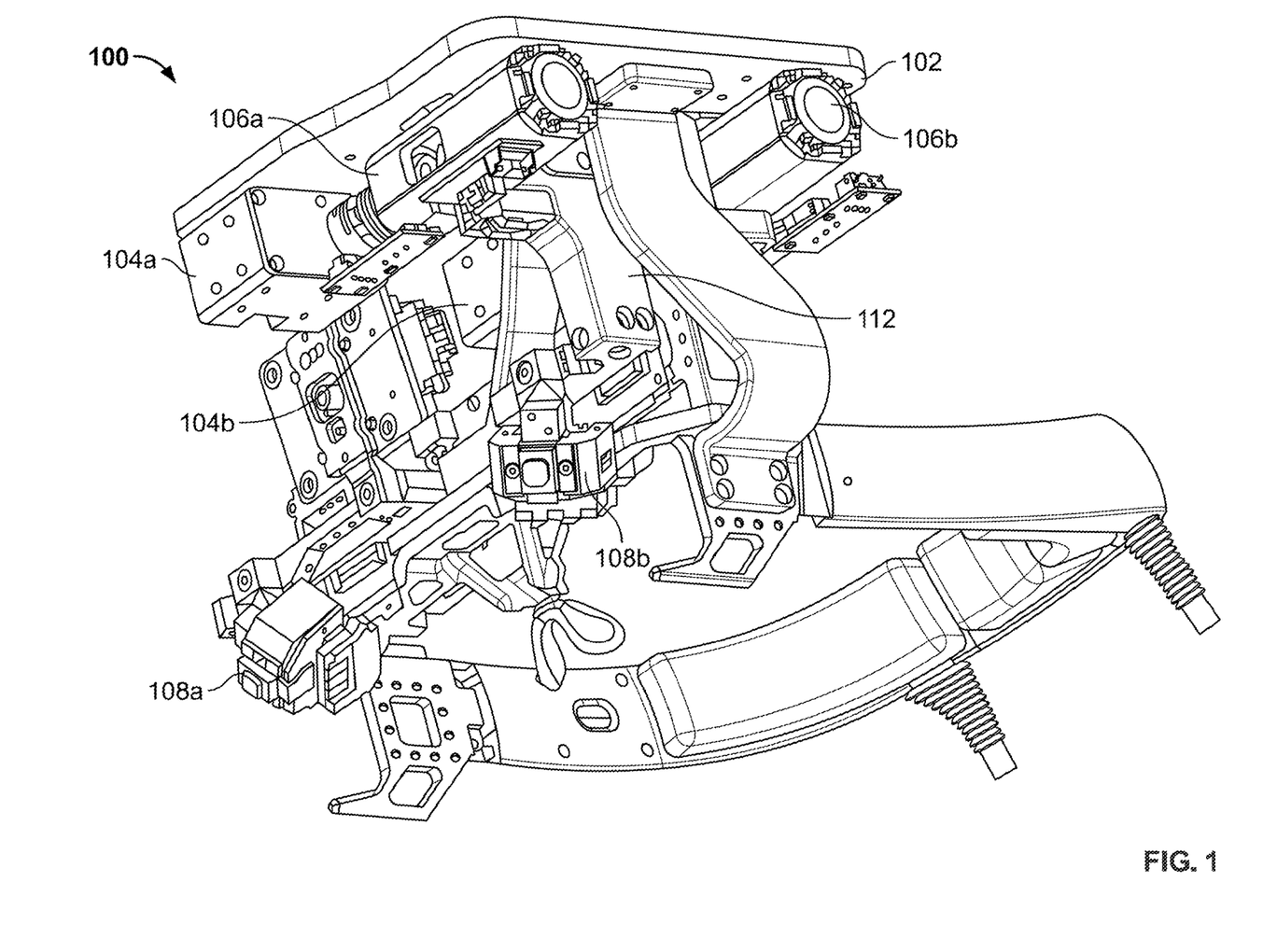
FIG. 1 shows a perspective view of an example displacement device, according to embodiments of the present disclosure.

FIG. 1 shows a perspective view of an example displacement device 100 in accordance with one or more embodiments of the present disclosure. As shown in the example of FIG. 1, the displacement device 100 can include various components to adjust the position of a tool (e.g., a camera, a sensor, or a combination of both). In some embodiments, the displacement device 100 can achieve a positional accuracy of the tool between about 0.1 microns (μm) to about 1 μm. In this example, displacement device 100 is coupled with a first camera 108a and a second camera 108b. In some embodiments, example displacement devices of the disclosure are coupled with one or more sensors. In some examples, the one or more sensors can include a head-mounted display sensor, an inertial sensor, a magnetic tracking sensor, an optical tracking sensor, an acoustic tracker sensor, an accelerometer, a gyroscope, a wireless tracking sensor, or any combination thereof. In some embodiments, example displacement devices of the disclosure are coupled with one or more lasers that enable the displacement devices to track and/or adjust the angular and/or linear position of a tool (e.g., a camera). The displacement device 100 can include a carriage 102 that can be coupled to a first bearing assembly 106a and a second bearing assembly 106b. Carriage 102 can be configured to support the tool (e.g., a camera, a sensor, or a combination of both). In some examples, carriage 102 has a substantially square shape with sides measuring about 140 millimeters (mm) to about 150 mm. In some embodiments, carriage 102 has a rectangular shape, a circular shape, or any other suitable shape that can accommodate the remaining components of the displacement device. In some embodiments, the tool can be mounted onto the carriage 102. For example, carriage 102 can include a mounting bracket 112 that is configured to attach the tool to the carriage 102. Mounting bracket 112 can be attached to a bottom surface of carriage 102, as shown in FIG. 1. In some embodiments, the mounting bracket is configured to attach the tool to the carriage 102 via fasteners (e.g., screws). In some examples, the tool is removably coupled to the carriage via mounting bracket 112. First and second bearing assemblies 106a and 106b can be coupled to a first and second motors 104a and 104b, respectively.

Figure 2:
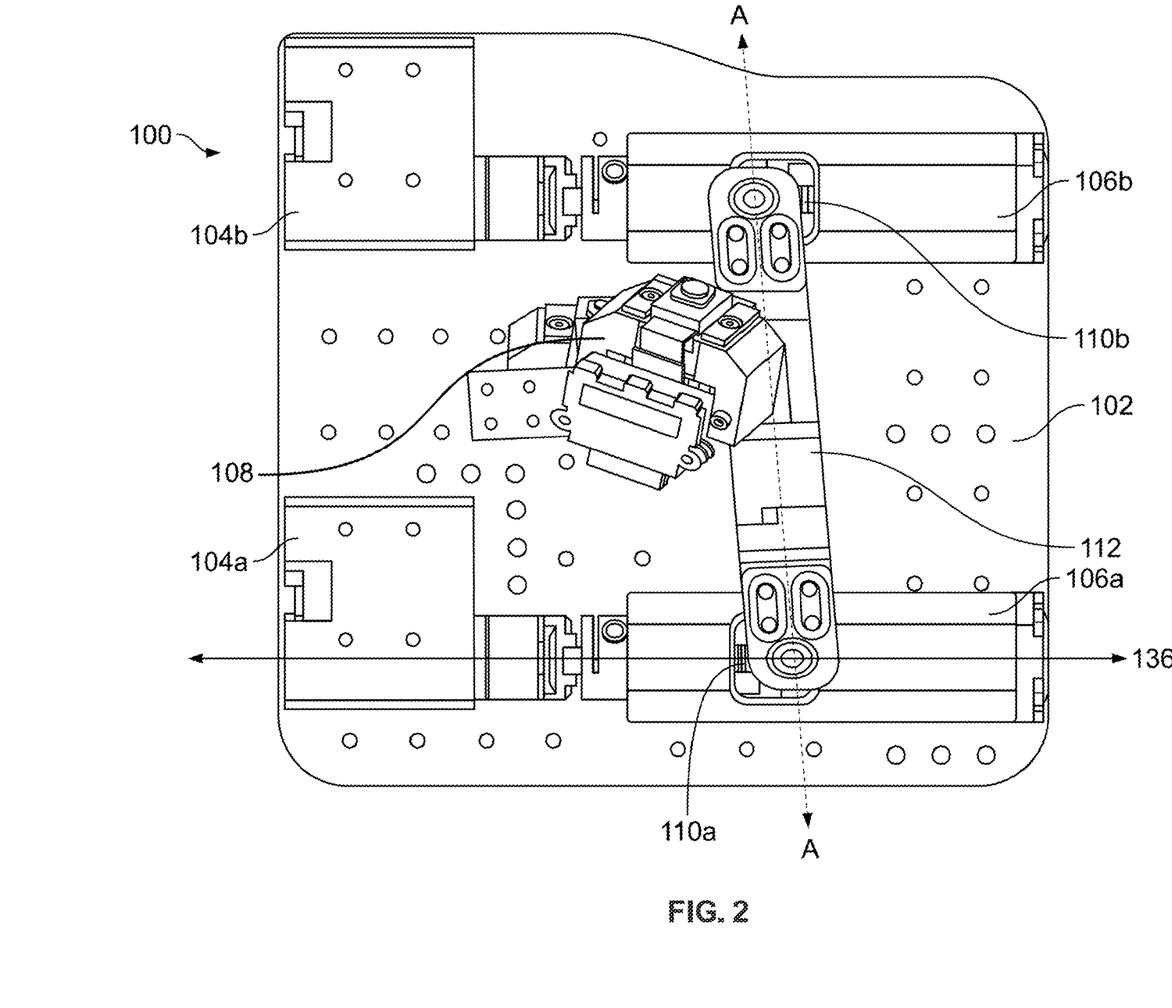
FIG. 2 shows a bottom view of an example displacement device, according to embodiments, of the present disclosure.

FIG. 2 shows a bottom view of an example displacement device 100, according to one or more embodiments of the present disclosure. The first and second bearing assemblies 106a and 106b and the first and second motors 104a and 104b can be attached to a bottom surface of carriage 102, as shown in this example of FIG. 2. For example, carriage 102 can include one or more holes that can receive one or more fasteners for removable attachment of various components (e.g., bearing assemblies and motors). In some embodiments, the bearing assemblies and motors are reversibly attached to carriage 102. In some examples, the bearing assemblies and motors are attached to carriage 102 via fasteners (e.g., screws). The first bearing assembly 106a can be arranged generally parallel to the second bearing assembly 106b, at opposing sides of carriage 102, as shown in FIG. 2. However, any other suitable arrangement of the bearing assemblies can be included in the design of this example displacement device. First and second bearing assemblies 106a and 106b permit a movement of the carriage 102 with respect to the first and second threaded shafts 110a and 110b. Threaded shafts 110a and 110b (and thus, each of their shaft axes 136) can be parallel to each other, as shown in FIG. 2. Movement of the carriage 102 further allow the position of the tool (e.g., a camera 108, a sensor, or a combination of both) to be adjusted. Displacement device 100 can further include a first threaded shaft 110a and a second threaded shaft 110b having a shaft axis 136 extending along their length, as shown in this example. First and second threaded shafts 110a and 110b can be disposed within and be coupled to the first and second bearing assemblies 106a and 106b, respectively. First and second motors 104a and 104b are configured to actuate the first and second shafts threaded 110a and 110b, respectively. Thus, first and second motors 104a and 104b are operatively coupled to the first and second threaded shafts 110a and 110b.

In some embodiments, the threaded shafts 110a and 110b include high density threads that enable the magnification of the motor accuracy. The high density threads of the threaded shafts 110a and 110b enable the devices of the disclosure to achieve sub-arcminute deformations in rotation and sum-millimeter deformations in translation. First and second threaded shafts 110a and 110b can be screws. In some embodiments, the screws are adjustment screws (e.g., fine adjustment screws). In some examples, the threaded shafts 110a and 110b are screws with threads ranging from about 40 to about 100 threads per inch (TPI). In some examples, the first and second threaded shafts 110a and 110b have a pitch of about 80 TPI. In some examples, the fine adjustment screws are screws with a pitch ranging from about 0.025 inches (in.) per revolution to about 0.01 in. per revolution (e.g., about 0.0125 in. per revolution). In some embodiments, first and second shafts threaded 110a and 110b are fine adjustment screws, ultra-fine adjustment screws, or a combination thereof. In some examples, ultra-fine adjustment screws are a screws with threads ranging from about 100 to about 508 threads per inch (TPI) (e.g., about 127, 200, or 254 TPI). In some examples, the ultra-fine adjustment screws are screws with a pitch ranging from about 0.01 inches (in.) per revolution to about 0.001 in. per revolution (e.g., 0.0079, 0.005, 0.0039, 0.00197 in. per revolution). In some examples, the first and second threaded shafts 110a and 110b have a pitch of about 0.0125 in. per revolution. First and second shafts threaded 110a and 110b can have a length ranging from about 0.375 inches to about 4 inches (e.g., 0.5, 0.75, 0.85, 1, 1.16, 1.5, 2, 3 inches or more). In some examples, the first and second shafts threaded 110a and 110b have a length of about 3 inches. First and second threaded shafts 110a and 110b can have a diameter ranging from about 0.1875 inches to about 1 inch (e.g., 0.5, 0.75, 0.85 inches or more). In some examples, the first and second threaded shafts 110a and 110b have a diameter of about 0.25 inches. In some embodiments, first and second threaded shafts 110 and 110b can be fabricated from stainless steel (e.g., 303 stainless steel). First and second threaded shafts 110a and 110b can include a ball tip configured to provide a single point contact for a surface being displaced. In some embodiments, the ball tip can be constructed using 440 stainless steel. In some embodiments, the ball tip contacts a stainless steel plate to prevent wear.

Figure 3:
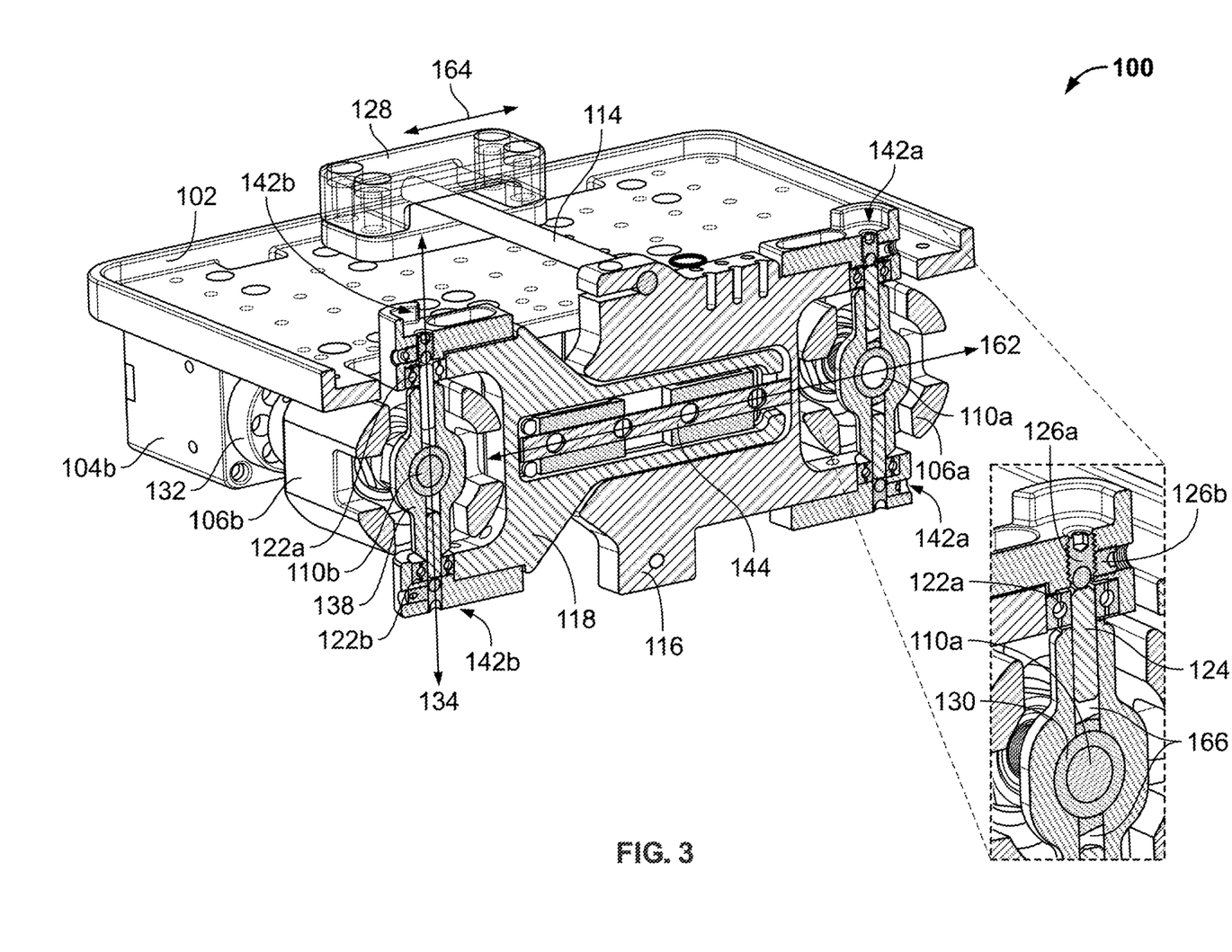
FIG. 3 shows a cross-sectional view along line A-A of FIG. 2 of an example displacement device, according to embodiments of the present disclosure.

FIG. 3 shows a perspective, cross-sectional view along line A-A of FIG. 2 of an example displacement device 100, according to embodiments of the present disclosure. Displacement device 100 can include a linear bearing 144 that is coupled to carriage 102 via a first carriage plate 116 and a second carriage plate 118. In some embodiments, linear bearing 144 is a telescoping slide. Linear bearing 144 can include a telescoping slide that translates horizontally, in the direction of linear bearing axis 160. Linear bearing 144 can enable rotation of the carriage 102. For example, without linear bearing 144, the rigid material would prevent rotation and over-constrain the system. In some examples, carriage 102 rotates about rotation axis 134. First carriage plate 116 and second carriage plate 118 can have "C"-shaped ends (i.e., clevis brackets) that are suitable for coupling to first bearing clamps 142a and second bearing clamps 142b, respectively, as shown in the example in FIG. 3. In this manner, first carriage plate 116 and second carriage plate 118 can couple the linear bearing 144 to the first and second bearing assemblies 106a and 106b. Furthermore, first carriage plate 116 and second carriage plate 118 can couple the first and second bearing assemblies 106a and 106b to carriage 102. A stabilizer bar 114 can couple the linear bearing 144 to carriage 102 via the first carriage plate 116. That is, stabilizer bar 114 couples to the first carriage plate 116 and further couples to a stabilizer bushing 128. The stabilizer bushing 128 includes top and bottom surfaces that can be machined from acetal plastic (e.g., Delrin) or other suitable materials. Stabilizer bushing 128 includes an opening that receives stabilizer bar 114 and allows movement of stabilizer bar in a horizontal direction as indicated by the double-sided arrow 164 in FIG. 3. In doing so, stabilizer bar 114 prevents potential movement constraints of carriage 102 in an axial direction. In some embodiments, stabilizer bar 114 can be composed of stainless steel or other suitable materials. In some embodiments, first carriage plate 116 and second carriage plate 118 can be composed of aluminum (e.g., 6061-T6 aluminum), stainless steel, plastic, or other suitable materials.

First bearing assembly 106a may be substantially similar in construction and function to second bearing assembly 106b. For example, first and second bearing assemblies 106a and 106 may include similar components arranged in substantially the same manner. First and second bearing assemblies 106a and 106b can be coupled to the first and second motors 104a and 104b via a motor coupling 132. As shown in FIG. 3, second bearing assembly 106b includes second bearing clamps 142b that couple a first bearing 122a and a second bearing 122b to the first carriage plate 116 and the second carriage plate 118. The first and second bearings 122a and 122b can attach the threaded shaft 110 to linear bearing 144 further coupled to the carriage 102, via the first carriage plate 116 and the second carriage plate 118.

As shown in the enlarged view of first bearing clamp 142a in FIG. 3, the pin 124 extends through the first bearing 122a and is held in place vertically via a first set screw 126a and second set screw 126b. First set screw 126a presses down on pin 124 in the direction of rotation axis 134. Second set screw 126b is disposed orthogonally with respect to the first set screw 126a to prevent first set screw 126a from loosening. In some embodiments, second set screw 126b adds stability and supports the first set screw 126a. First bearing clamp 142a is clamped around first bearing 122a using fasteners (e.g., screws) through slots in the top surface to securely hold the bearing in place.

First and second bearing assemblies 106a and 106b can include bearing mounts 138. Bearing mounts 138 are generally disposed orthogonally with respect to the shaft axis. In other words, bearing mounts 138 can be generally aligned with the rotation axis 134. Bearing mount 138 has a continuous vertical through-hole 166 into which two separate pins 124 are press fit to act as bearing shafts for first and second bearings 122a and 122b. One or more nuts 130 can fasten and help secure threaded shaft 110 to bearing mount 124. In some examples, nuts 130 can be composed of brass or other suitable materials. Pin 124 may be received by recess 166 of bearing mount 138. Pin 124 can extend from the recess 166, into the bore of first bearing 122a, and finally abut an end portion of first set screw 126a. In some embodiments, pin 124 can be composed of stainless steel or other suitable materials. In some examples, first and second bearing clamps 142a and 142b can be composed of stainless steel, plastic, or other suitable materials. In some examples, bearing mount 138 can be composed of aluminum or other suitable material. In this example, the components attaching to both end portions of the bearing mount 138, can be substantially similar to each other. For example, bearing mount 138 may receive a substantially similar pin 134 in both of its recesses 166, first and second bearings 122a and 122b may be substantially similar in construction and may attach to the bearing mount 138 and the bearing clamps in a substantially similar manner.

Figure 4:
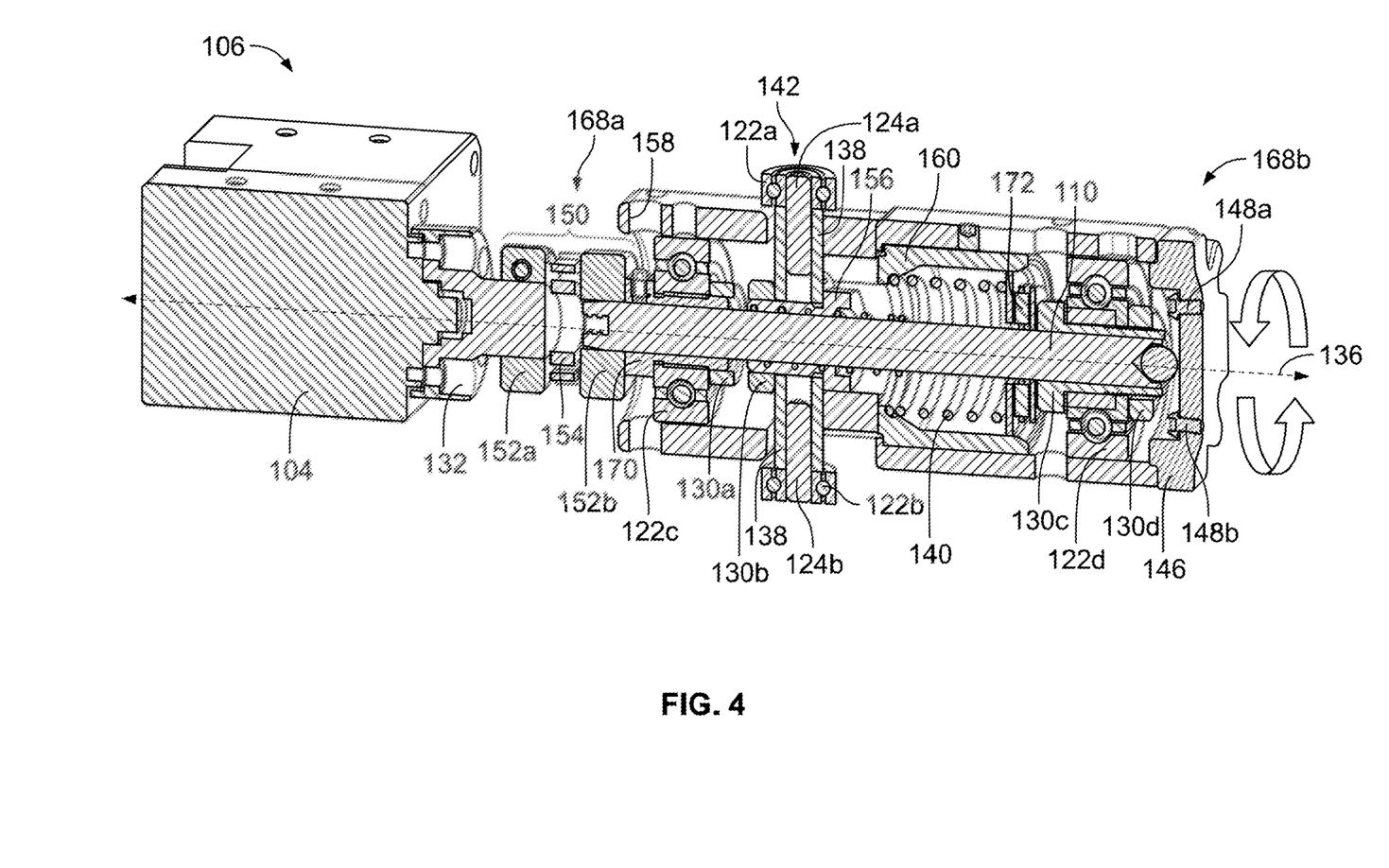
FIG. 4 shows a cross-sectional view of an example bearing assembly included in an example displacement device, according to embodiments of the present disclosure.

FIG. 4 shows a cross-sectional view of an example bearing assembly 106 included in an example displacement device, according to embodiments of the present disclosure. Displacement devices of the disclosure can include a threaded shaft 110 having a first end 168a, a second end 168b, and a shaft axis 136 extending therebetween. Bearing assembly 106 can be coupled to threaded shaft 110, as shown in FIG. 4. Motor 104 actuates rotation of threaded shaft 110 about shaft axis 136, as indicated by the curved arrows. Motor 104 can be operatively coupled to threaded shaft 110 via motor coupling 132 and shaft coupling 150. For example, motor 104 can be coupled to a motor coupling 132 which is further coupled to the shaft coupling 150, which further couples to threaded shaft 110, as shown in this example.

Motor coupling 132 can include a hub that couples to motor 104 one end and another hub that couples to shaft coupling 150 on the other end. In some embodiments, motor coupling 132 is an Oldham coupling. In some embodiments, motor coupling 132 is a high parallel misalignment flexible shaft coupling. In some embodiments, motor coupling 132 is composed of aluminum or other suitable materials. Motor coupling 132 can reduce or eliminate potential parallel misalignment of threaded shaft 110. Motor coupling 132 can further include clamping screws to axially secure the hubs onto motor 104 and shaft coupling 150.

Shaft coupling 150 can include a first and second hub 152a and 152b, respectively, and a disc 154 sandwiched in between the first hub 152a and the second hub 152b. In some embodiments, shaft coupling 150 is a Schmidt coupling. In some examples, shaft coupling 150 is a high angular misalignment flexible shaft coupling. In some embodiments, shaft coupling 150 is composed of aluminum or other suitable materials. Shaft coupling 150 can reduce or eliminate potential angular misalignment of threaded shaft 110. Shaft coupling 150 can further include clamping screws to axially secure the first and second hubs 152a and 152b and disc 154 onto threaded shaft 110. In some embodiments, shaft coupling 150 can clamp evenly around the first end 168 of threaded shaft 110 for a mar-free hold.

The majority of the remaining components of the bearing assembly 106 can be housed within bearing assembly housing 158, as shown in FIG. 4. For example, a third bearing 122c and a fourth bearing 122d can be disposed within bearing assembly housing 158. Shaft coupling 150 can couple to the third bearing 122c via coupling 170. Third and fourth bearings 122c and 122d can axially attach to the threaded shaft 110. In other words, threaded shaft 110 can extend from the shaft coupling 150 and into the bores of the third and fourth bearings 122c and 122d. First nut 130a, third nut 130c, and fourth nut 130d can help secure the third and fourth bearings 122c and 122d to the threaded shaft 110. The third and fourth bearings 122c and 122d can be configured to enable rotation of the threaded shaft 110 while reducing friction between an outer surface of the threaded shaft and an inner surface of the third and fourth bearings. Thus, in some embodiments, third and fourth bearings 122c and 122d allow a substantially frictionless rotation of threaded shaft 110 about shaft axis 136.

As described elsewhere herein, bearing assembly 106 can include a bearing clamp 142 and bearing mount 138 that orthogonally attach to the threaded shaft 110. Adjuster 156 and second nut 130b can be axially coupled to threaded shaft 110 while also coupling the bearing mount 138 to threaded shaft 110. Bearing assembly 106 can include a spring 140 disposed within a spring housing 160. Spring 140 can bias the bearing assembly 106, including threaded shaft 110, along the shaft axis 136. Spring 140 can be generally coaxial with threaded shaft 110 and can couple threaded shaft 110 via a thrust bearing 172. In some examples, threaded shaft 110 is spring-loaded in an axial direction against a surface of the bearing assembly 106. In some embodiments, the surface is an inner surface of end cap 146. In some embodiments, the surface is a disc abutting the inner surface of end cap 146. For example, a distal end 168b of threaded shaft 110 can contact the inner surface of end cap 146. End cap 146 can be attached to housing 158 via first screw 148a and second screw 148b.

Figure 5:
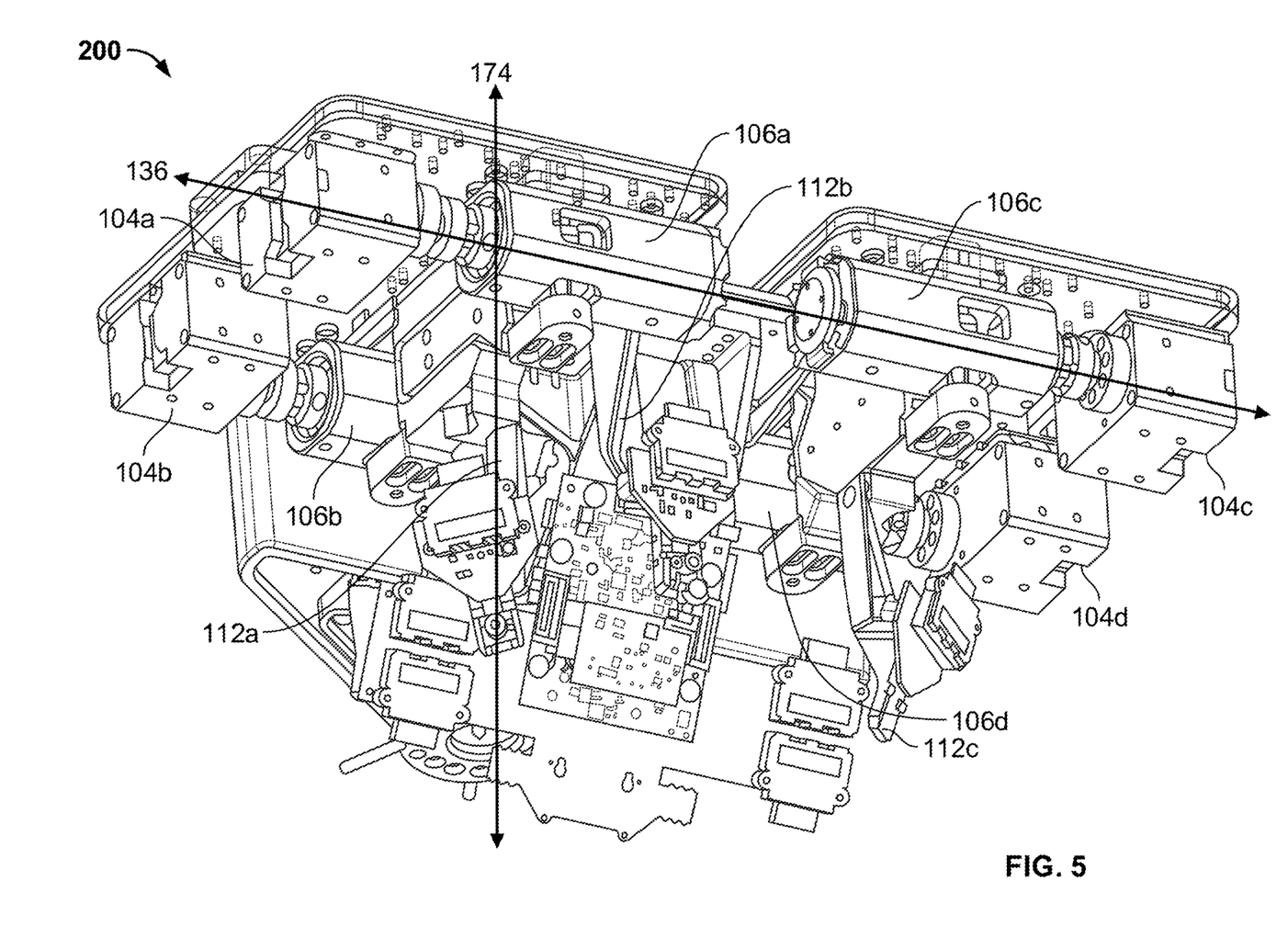
FIG. 5 shows a perspective view of an example displacement device including two sets of bearing assemblies, motors, threaded shafts, and carriages, according to embodiments of the present disclosure.

In some embodiments, example displacement devices include only one bearing assembly, one threaded shaft, one motor, and one carriage. In other examples, displacement devices include two bearing assemblies, two threaded shafts, two motors, and one carriage. In further embodiments, example displacement device 200 can include four bearing assemblies (106a, 106b, 106c, and 106d), four threaded shafts, four motors (104a, 104b, 104c, and 104d), and two carriages (102a and 102b), as shown in FIG. 5. Displacement device 200 can include a first, second, and third mounting bracket 112a, 112b, and 112c that can couple one or more tools (e.g., 1, 2, or 3 cameras, sensors, or a combination of both) to displacement device 200.

In some embodiments, example displacement devices can be part of an automated system for adjusting a position of a tool (e.g. a camera, a sensor, or a combination of both). The automated system can further include a computing device including a processor operatively coupled to the example displacement devices of the disclosure. The automated system can include a non-transitory computer readable storage medium with a computer program including instructions executable by the processor. These instructions can cause the processor to, for example, calculate a rotation of the threaded shaft along the shaft axis that results in a desired position of the camera along the shaft axis, and ii) output the rotation of the threaded shaft to the motor.

In some embodiments, the position of the tool (e.g., a camera) includes an angular position that can define an initial angle of the tool that is mounted on an example displacement device of the disclosure. The angle of the tool (e.g., a camera) can be defined by camera axis 174 and shaft axis 136. For example, when the tool is perpendicular to shaft axis 136 (i.e., parallel to camera axis 174), the angle of the tool (e.g., a camera) is 0 degrees. As shown in FIG. 5, camera axis 174 perpendicularly traverses the shaft axis 136. The position of the mounted tool can include a linear position with respect to the shaft axis. In some examples, the processor of the automated system can calculate a desired angle of the tool relative to the initial angle of the tool based on the rotation of the screw. In further embodiments, the processor can further calculate a desired linear position of the mounted tool relative to an initial linear position of the tool based on the displacement of the threaded shaft. Thus, controlling the rotation of the threaded shaft (e.g., a fine adjustment screw), at sub-millimeter and sub-arcminute scales, can enable a user to control the linear and angular position of a tool mounted on an example displacement device of the disclosure with high accuracy. In some embodiments, the high accuracy, as used herein, can be defined as a positional accuracy ranging between about 0.1 microns (μm) to about 1 μm.

While this specification contains many specific details, these should not be construed as limitations on the scope of the disclosure or of what may be claimed, but rather as examples of features that are associated with particular embodiments. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some examples be excised from the combination, and the claimed combination may be directed to a sub-combination or variation of a sub-combination.

A number of embodiments have been described. Nevertheless, it will be understood that various modifications may be made without departing from the spirit and scope of the disclosure. For example, various structures shown above may be used, with elements rearranged, positioned differently, oriented differently, added, and/or removed. Accordingly, other embodiments are within the scope of the following claims.

What is claimed is:

1. A device for adjusting a position of a camera, the device comprising:
   a threaded shaft having a first end and a second end and a shaft axis extending therebetween;
   a motor that actuates the threaded shaft to move in a direction of the shaft axis, the motor being operatively coupled to the threaded shaft;
   a carriage coupled to the camera;
   a linear bearing coupled to the carriage; and
   a bearing assembly coupled to the threaded shaft and the carriage, the bearing assembly comprising a first bearing and a second bearing attaching the threaded shaft to the linear bearing thereby enabling rotation of the carriage, the bearing assembly permitting a movement of the carriage with respect to the threaded shaft,
   wherein the movement of the carriage allows the position of the camera to be adjusted.

2. The device of claim 1, wherein the threaded shaft is a screw.

3. The device of claim 2, wherein the screw is a fine adjustment screw.

4. The device of claim 3, wherein the fine adjustment screw comprises about 80 to about 100 threads per inch.

5. The device of claim 1, wherein the device comprises a positional accuracy of the camera of about 0.1 micrometers (μm) to about 1 μm.

6. The device of claim 1, wherein a stabilizer bar couples the linear bearing to the carriage.

7. The device of claim 1, wherein the bearing assembly comprises a third bearing and a fourth bearing axially attached to the threaded shaft, the third and fourth bearings configured to enable rotation of the threaded shaft while reducing friction between an outer surface of the threaded shaft and an inner surface of the third and fourth bearings.

8. The device of claim 1, wherein the camera is removably coupled to a bracket of the carriage.

9. The device of claim 1, wherein the bearing assembly comprises a spring for biasing the bearing assembly along the shaft axis, the spring being generally coaxial with the shaft axis.

10. The device of claim 9, further comprising a thrust bearing coupling the threaded shaft to the spring.

11. The device of claim 9, wherein the threaded shaft is spring-loaded in an axial direction against a surface of the bearing assembly.

12. The device of claim 1, wherein the position of the camera comprises an angular position, a linear position with respect to the shaft axis, or a combination thereof.

13. The device of claim 1, wherein the motor actuates the threaded shaft to rotate with respect to a camera axis, the camera axis perpendicularly traversing the shaft axis.

14. The device of claim 1, further comprising a threaded nut coupling the threaded shaft to the carriage.

15. The device of claim 1, further comprising:
an additional threaded shaft having a first end and a second end and an additional shaft axis extending therebetween;
an additional motor that actuates the additional threaded shaft to move in a direction of the additional shaft axis, the additional motor being operatively coupled to the additional threaded shaft;
an additional carriage coupled to an additional camera; and
an additional bearing assembly coupled to the additional threaded shaft and the additional carriage, the additional bearing assembly permitting a movement of the additional carriage with respect to the additional threaded shaft;
wherein the movement of the additional carriage allows the position of the additional camera to be adjusted.

16. An automated system for adjusting a position of a camera, the automated system comprising:
a device comprising:
a threaded shaft having a first end and a second end and a shaft axis extending therebetween;
a motor that actuates the threaded shaft to move in a direction of the shaft axis, the motor being operatively coupled to the threaded shaft;
a carriage coupled to the camera,
a linear bearing coupled to the carriage; and
a bearing assembly coupled to the threaded shaft and the carriage, the bearing assembly comprising a first bearing and a second bearing attaching the threaded shaft to the linear bearing thereby enabling rotation of the carriage, the bearing assembly permitting a movement of the carriage with respect to the threaded shaft,
wherein the movement of the carriage allows the position of the camera to be adjusted; and
a computing device comprising a processor operatively coupled to the device, and a non-transitory computer readable storage medium with a computer program including instructions executable by the processor causing the processor to: i) calculate a displacement of the threaded shafts along the shaft axis that results in a desired position of the camera along the shaft axis, and ii) output the displacement of the threaded shaft to the motor.

17. The automated system of claim 16, wherein the position of the camera comprises an angular position defining an initial angle of the camera.

18. The automated system of claim 17, wherein the position of the camera comprises a linear position with respect to the shaft axis.

19. The automated system of claim 17, wherein the processor further calculates a desired angle of the camera relative to the initial angle of the camera based on the displacement of the threaded shaft.

* * * * *